(12) United States Patent
Farrell

(10) Patent No.: US 10,898,369 B2
(45) Date of Patent: Jan. 26, 2021

(54) ORAL APPLIANCE

(71) Applicant: Myosa Pty Ltd, Helensvale (AU)

(72) Inventor: Christopher John Farrell, Helensvale (AU)

(73) Assignee: Myosa Pty Ltd

( * ) Notice: Subject to any disclaimer, the term of this patent is extended or adjusted under 35 U.S.C. 154(b) by 320 days.

(21) Appl. No.: 15/819,197

(22) Filed: Nov. 21, 2017

(65) Prior Publication Data

US 2018/0078405 A1 Mar. 22, 2018

Related U.S. Application Data

(63) Continuation-in-part of application No. PCT/AU2016/000174, filed on May 20, 2016.

(30) Foreign Application Priority Data

May 22, 2015 (AU) ................................ 2015901890

(51) Int. Cl.
*A61F 5/56* (2006.01)
(52) U.S. Cl.
CPC .................................... *A61F 5/566* (2013.01)
(58) Field of Classification Search
CPC ...... A61F 5/56; A61F 5/566; A61F 2005/563; A61F 7/36; A61C 7/08; A63B 71/085; A63B 2071/086; A63B 2071/088
See application file for complete search history.

(56) References Cited

U.S. PATENT DOCUMENTS

| 6,055,986 A | 5/2000 | Meade |
| 6,295,988 B1 | 10/2001 | Sue |

(Continued)

FOREIGN PATENT DOCUMENTS

| EP | 1203570 A2 | 5/2002 |
| JP | 2009028389 A | 2/2009 |

(Continued)

OTHER PUBLICATIONS

Extended European Search Report including Written Opinion for EP16798936.7 dated Jan. 24, 2019.

*Primary Examiner* — Rachael E Bredefeld
*Assistant Examiner* — Camtu T Nguyen
(74) *Attorney, Agent, or Firm* — Lerner, David, Littenberg, Krumholz & Mentlik, LLP

(57) ABSTRACT

A method of treating sleep disorder breathing in a patient, the method comprising in a first step providing a set of oral appliances comprising a first and at least a second oral appliance (30). Each of the first and at least second oral appliances comprises a generally U shaped appliance body including an inner wall (34), an outer wall (36), and a web (38) interconnecting the inner wall and the outer wall. The web has a front section and two arms with trailing ends. The web comprises at least one breathing hole (80) so as to define a total cross sectional area for breathing and the total cross sectional area for breathing of the first oral appliance is larger than the total cross sectional area for breathing of the second oral appliance. In a second step, a patient wears the first oral appliance in a first treatment stage whilst sleeping for a first period of time and in a third step the patient wears the second oral appliance in a second treatment stage whilst sleeping for a second period of time.

6 Claims, 9 Drawing Sheets

(56) References Cited

U.S. PATENT DOCUMENTS

| | | | |
|---|---|---|---|
| 7,004,172 B1 * | 2/2006 | Zacco | A61F 5/566 |
| | | | 128/848 |
| 2006/0102171 A1 | 5/2006 | Gavish | |
| 2007/0149891 A1 | 6/2007 | George et al. | |
| 2008/0076094 A1 | 3/2008 | Hindin | |
| 2008/0236597 A1 | 10/2008 | Bergersen | |
| 2009/0241969 A1 | 10/2009 | Walker | |
| 2010/0018538 A1 * | 1/2010 | Sotos | A61F 5/566 |
| | | | 128/848 |
| 2010/0196837 A1 | 8/2010 | Farrell | |
| 2011/0168188 A1 | 7/2011 | Moore et al. | |
| 2012/0186589 A1 | 7/2012 | Singh | |

FOREIGN PATENT DOCUMENTS

| | | |
|---|---|---|
| WO | 9423674 A1 | 10/1994 |
| WO | 2015/123718 A1 | 8/2015 |

* cited by examiner

ORAL APPLIANCE

CROSS REFERENCE TO RELATED APPLICATIONS

This application is a continuation-in-part of International Application No. PCT/AU2016/000174 filed on May 20, 2016, which claims priority from Australian Patent Application No. 2015901890, filed May 22, 2015, the disclosures of which are incorporated herein by reference.

FIELD

The present disclosure relates broadly to an oral appliance for use in the treatment of sleep disorder breathing (SDB). The disclosure also relates broadly to a method of training a patient to nose breathe rather than mouth breathe.

The disclosure also extends to a system of appliances for treating a patient having SBD and/or training a patient to nose breathe rather than mouth breathe.

DEFINITIONS

In the specification and claims the term "comprising" shall be understood to have a broad meaning similar to the term "including" and will be understood to imply the inclusion of a stated integer or step or group of integers or steps but not the exclusion of any other integer or step or group of integers or steps. This definition also applies to variations on the term "comprising" such as "comprise" and "comprises".

In the specification and claims, the term "sleep disorder breathing" refers to any condition where there is an abnormal breathing pattern during sleep. In some cases this abnormality is as a result of an upper airway obstruction during sleep, including but not limited to include snoring, upper airway resistance syndrome (UARS), and obstructive sleep apnea-hypopnea syndrome (OSAHS). Abnormal breathing can also occur in the absence of any airway obstruction during sleep in which the patient stops breathing for a period of time, known as an apneic event.

BACKGROUND

Over the past two decades, the medical and dental profession has become more aware of breathing disorders and in particular sleep disorder breathing as a major contributor to a number of health problems. Previously it was considered that snoring was a manifestation of a sleeping habit but it is now known that this leads to more severe disorders like Obstructive Sleep Apnea (OSA). OSA has been associated with the causes of heart disease, strokes and all as chronic daytime tiredness and spontaneous sleeping. The various forms of severity of OSA, snoring, and other syndromes have been described under the definition Sleep Disorder Breathing (SDB).

SDB comprises a wide spectrum of sleep-related breathing abnormalities; those related to an increase in upper airway resistance include snoring, upper airway resistance syndrome (UARS), and obstructive sleep apnea-hypopnea syndrome (OSAHS). Many clinicians regard SDB as a spectrum of diseases. This concept suggests that a person who snores may be exhibiting the first manifestation of SDB and that snoring should not be viewed as normal. This concept has support from experimental studies showing increasing airway collapsibility during sleep with progression from normal, snoring, UARS, and OSA.

Snoring is one of the most common aspects of SDB. After sleep apnea syndrome was recognized, snoring began to be viewed as an important clinical symptom. Although it is by far the most common symptom of sleep apnea, not all patients who snore have sleep apnea.

Pathogenesis of OSA involves a combination of reduced upper airway size and altered upper airway muscle activity, which causes oral tissue to collapse, and hence a blockage to occur. When a person is awake, muscles hold the pharyngeal airway open. These muscles can relax when sleeping. Other factors which are thought to contribute to OSA include weight, tongue size, soft palate volume, a retrognathic mandible, an anteroposterior discrepancy between the maxilla and the mandible, and obesity.

Snoring and OSA are often associated as generally both are caused by blockage of the pharyngeal airway by, for example, excess tissue when various muscles of the body, including the tongue, relax. As the tongue relaxes, it moves posteriorly, blocking the pharyngeal airway. When the pharyngeal airway is blocked, exhaled air is forced through the airway with increased velocity thereby causing vibration of the tongue, tissue, or other obstruction, thereby creating noise.

Snoring is caused by the partial obstruction of breathing during sleep while OSA occurs when the tongue and soft palate collapse onto the back of the throat and completely block the pharyngeal airway, thereby stopping breathing during sleep and restricting the flow of essential oxygen. Thus, a correlation between snoring and OSA is generally recognized in the medical community.

Snoring is common in people who breathe through their mouth when asleep. Mouth breathing causes the mandible to drop and decreases the area of the pharyngeal airway. It also causes the tongue to be pushed back into the throat, thereby creating the obstruction associated with SDB The traditional medical treatment for OSA has been the Continuous Positive Air Pressure Appliance (CPAP). CPAP treatment uses a positive air pressure to hold the airway open during sleep. The positive air pressure is generated by a pump and is applied through a small mask which fits over the nose, or the nose and mouth. CPAP stops snoring by preventing structures in the airway from vibrating. Equally as important, CPAP prevents the airway from becoming narrow and obstructing breathing. When an optimal pressure is applied through the mask, breathing becomes regular and unobstructed, the body's oxygen levels remain stable and the patient does not snore.

CPAP however, does not cure obstructive sleep apnoea—it only treats the symptoms of OSA. Therefore, if patients cease using CPAP, snoring and obstructive sleep apnoea will usually return. For this reason, CPAP treatment must be used every night. CPAP is also a bulky, inconvenient and uncomfortable method of treatment, causing the majority patients to stop treatment and live with the complaint.

Intra-Oral appliances for alleviation of SDB symptoms have been used for a similar period to the CPAP. While considered less effective and not suitable for more severe cases, they are more convenient, easier to use and certainly more portable. So the compliance factor has brought the attention of the medical profession to view intra-oral appliances as the primary treatment for SDB for moderate to more severe cases who have a compliance issue with the CPAP regime.

There are many types of Dental Sleep Appliances (DSA) and the designs vary considerably. The most common are the Mandibular Advancement Devices (MAD). The principle behind the MAD devices is that advancing the mandible in an anterior position relative to the maxilla during sleep opens the pharyngeal airway by indirectly urging the tongue forward to stimulate activity of the muscles in the tongue and thereby also increases the forward rigidity of the tongue. Since the tongue attaches to the posterior portion of the mandibular symphysis, advancing the mandible forward relative to the maxilla also pulls the tongue forward, thus preventing the tongue from obstructing the pharyngeal airway. Mandibular advancement devices therefore function to move the mandible, and hence the tongue forward to open the oropharynx. Snoring is believed to decrease proportionally with the increase in airway size or diameter.

One type of MAD is a single piece double mouth guard like device that fits to the upper and lower teeth. It is considered important that these devices allow essentially unrestricted breathing through the mouth. The reason behind this is that if the problem is an obstructed airway, that restricting air flow through the mouth will be counterproductive.

Other MAD devices are in two parts that are hinged that are adjustably connectable to allow for titration of the amount of advancement. Others are formed from a single piece of thermoplastic with a living hinge. A recognized advantage of the hinged devices is that they allow the mouth to open for unrestricted breathing. It is considered very important that breathing is not restricted for mouth breathers as the object of the prior art MAD devices is to increase the amount of airflow.

However, these MAD devices pose potentially damaging effects. Most single piece devices fit over both the maxillary and mandibular teeth and are typically held nearly stationary, thereby restricting movement, causing discomfort, and potential permanent repositioning of the jaw.

The temporomandibular joint (TMJ) is the joint that connects the mandible to the skull. The mandibular condyle is received within the superior synovial cavity The TMJ is flexible, allowing the mandible to move smoothly up and down and side to side and enabling a person to talk, chew and yawn. Muscles attached to and surrounding the TMJ control the position and movement of the mandible.

Continued use of devices that restrict the natural lateral movements as well as anterior and posterior movement of the mandible can potentially aggravate the TMJ and the related facial musculature.

Still further, mandibular advancement will clearly place stress on the TMJ as the mandibular condyle is anteriorly displaced relative to its normal position. This can lead to TMJ disorder. TMJ disorder covers a group of conditions that cause pain and dysfunction in the jaw joint and the muscles that control jaw movement.

There are therefore serious concerns within the dental community of the medium to long term effects of devices that over advance the mandible. These effects can cause adverse changes in occlusion, damage teeth and potential damage to the TMJ's. However, it is thought that the high priority in correcting snoring, SDB and health issues from OSA would make the medical practitioner and patient consider this a side effect that needs to be accepted for the overall benefits.

Patients with existing TMJ disorders are generally cautioned against using a MAD as such use can exacerbate the condition. A healthy TMJ is a prerequisite for MAD use.

MADs are based on orthodontic appliance principles which are designed to correct a class II malocclusion. In a class II malocclusion there is a misalignment between the teeth of the dental arches and the upper teeth are forward of the lower teeth in what is commonly known as an overbite.

Orthodontic appliances for the treatment of class II malocclusions in pre-adolescents advance the mandible and stimulate and enhance mandibular growth. The appliances also place an equal and opposite retractive force on the maxilla and restrains growth of the maxilla.

It is generally believed that the greater level of mandibular advancement caused by a MAD, the better the treatment effective for SDB. Advancement of between 50% and 75% of maximum mandibular protrusions is recommended. Physiological protrusion lengths are typically between about 7 mm to about 12 mm. The American Academy of Dental Sleep Medicine (AADSM) has published a report on what features define an effective oral appliance for the treatment of OSA. One of the features defined is that the appliance should permit protrusive advancement over a range of at least 5 mm. It is considered desirable to be able to gradually advance the mandible with treatment so as to reduce pain and soreness and alleviate TMJ pain.

These recommendations have been based upon a number of factors and in particular pulse oximetry. Oximetry measures hemoglobin $O_2$ saturation. This measurement is based upon the generally held belief in the MAD art that simply physically opening up the airways and allowing more air to be breathed can treat SDB.

It may be appreciated that using an oral appliance designed for treating a class II malocclusion by advancing the mandible and retracting the maxilla would have the same effect on a person with normal occlusion.

It is the maxilla that determines the effective horizontal dimension of the pharynx and in particular the upper pharynx. Maxillary constriction has been reported to be associated with narrowing of the pharyngeal airway and may play a role in the etiology of OSA. Rapid maxillary expansion is an effective procedure for widening nasal cavities and decreasing nasal airway resistance which can lead to improvement in nasal breathing.

Furthermore, it can be a useful therapy in children with obstructive sleep apnea syndrome.

Long term mandibular advancement for a patient having a normal occlusion towards a non-physiological position that retracts the maxilla may cause maxilla contraction. As the maxilla accommodates the nasal passages, this also may cause constriction of the nasal passages, thereby encouraging the mouth breathing that contributes to the problem.

Using a device to alleviate SBD symptoms that may promotes the possible causative effect of OSA of narrowing the pharyngeal airway is bound to cause difficulties. The patient's SBD symptoms will be worse off when not wearing the appliance. In order to alleviate symptoms, the patient must wear the appliance indefinitely.

SDB including snoring and OSA is also very common in childhood often begins when adenotonsillar enlargement peaks in the 2-5 year old age range. The American Academy of Sleep Medicine reports that the prevalence of OSA is approximately two percent in otherwise healthy young children. Chronic snoring occurs in almost 10% of children of both sexes.

Children with SDB present with behaviour problems, deficits of general intelligence, learning and memory deficits, evidence of brain neuronal injury, increased cardiovascular risk, and poor quality of life. Children are in a rapid state of cognitive development; therefore, alterations of health and brain function associated with SDB could permanently alter a child's social and economic potential, especially if the disorder is not recognized early in life or is treated inadequately.

One treatment for OSA in infants and children is surgical removal of tonsils and adenoids. However, treatment with CPAP therapy is increasingly being used. The main concern in using CPAP on children is the potential of the mask and headgear to cause structural changes in the face and restrict forward facial growth with long-term use. The bones in the face are not fused in children and so are malleable.

Additionally, MAD devices cannot be used on growing children as they can have major detrimental effects on orofacial growth and development. Forcing the mandible forward can result in class 3 malocclusion in which the mandible is more developed than the maxilla and does not correctly match the size of the upper arch. In children whose OSA is associated with maxillary constriction, the MAD devices would make a bad situation significantly worse.

Still further, the MAD devices protrude the mandible by applying force on a patient's teeth. Patients must therefore have healthy, well supported and distributed teeth that can withstand the force.

As a result of the force applied to the teeth, long term MAD use i.e. three or more years may lead to retroinclination of the maxillary incisors, proinclination of the mandibular incisors, a decrease in the number of occlusal connect points, an anteroposterior change on occlusion, increases in the mandibular plane angle and increases in the anterior facial height.

It is well established that the use of intraoral appliances for SDB therapy is an ongoing process. The appliances simply treat the symptoms without in any way addressing the underlying cause. The American Academy of Dental Sleep Medicine (AADSM) recommends that an oral appliance must have an expected lifespan of at least three years.

Other devices are known as tongue retaining devices that work by pulling the tongue forward so as to open the airway, with less or no mandibular advancement when compared with the MAD devices. It will be appreciated that by pulling the tongue forward, it is also not possible to mouth breath and/or many devices block the mouth completely. Such devices are uncomfortable and have poor compliance.

It may be appreciated that all of the above appliances and treatments attempt to ameliorate the symptoms of SDB by seeking to open up the pharyngeal airway by applying external physical force. However, they fail to address any solution to the problem, or in any way suggest that a solution is possible.

Mouth breathing is also considered a breathing disorder that has a number of detrimental effects that are well documented, particularly in growing children. Poor oral posture and habits in a growing child can cause a number of problems such as malocclusion, crowing of the teeth, an open bite and narrow arch formations. These problems can adversely affect facial growth patterns. Failure to treat these problems at an early age in a growing child will generally require physical intervention such as braces and/or surgery at a later date. This is a most undesirable outcome for a patient. Current treatments for mouth breathing concentrate on myofunctional therapy.

SUMMARY OF THE DISCLOSURE

The present disclosure therefore relates to a method of treating sleep disorder breathing in a patient, the method comprising the steps of;

(a) providing a set of oral appliances comprising a first oral appliance and at least a second oral appliance, wherein each of the first oral appliance and at least second oral appliance comprises;

a generally U shaped appliance body with a front section and two arms, the appliance body including an inner wall and an outer wall, a web interconnecting the inner wall and the outer wall, the web having a front section and two arms with trailing ends, each of the inner wall and outer wall have an upper portion that projects above the web so as to define an upper dental arch receiving channel;

each of the inner wall and the outer wall have a lower portion that depends from the web so as to define a lower dental arch receiving channel; and wherein the web comprises at least one breathing hole so as to define a total cross sectional area for breathing and the total cross sectional area for breathing of the first appliance is larger than the total cross sectional area for breathing of the second oral appliance;

(b) causing the patient to wear the first oral appliance in a first treatment stage whilst sleeping for a first period of time; and (c) causing the patient to wear the second oral appliance in a second treatment stage whilst sleeping for a second period of time.

This method is based upon an understanding of the biochemistry and physiology of ventilation and the critical role that is played by $CO_2$. It may be appreciated that this is an entirely different approach to prior art MAD devices that are only concerned with physically opening up the airways by advancing the mandible or using tongue retaining devices that hold the tongue forward.

The human respiratory control system operates such that under normal conditions the respiratory and circulatory systems deliver $O_2$ according to metabolic demands and excrete $CO_2$ in the amount that it is generated. Excretion of $CO_2$ plays a significantly more important role than merely removal of a waste gas.

$CO_2$ is enzymatically converted to carbonic acid in the blood stream which in turn dissociates to hydrogen ion and bicarbonate buffer;

$$CO_2 + H_2O \rightarrow H_2CO_3 \rightarrow H^+ + HCO_3^-$$

$CO_2$ therefore plays a critical role in plasma pH control.

Oxygen haemoglobin dissociation is pH dependent. An increase in pH increases haemoglobin's affinity for $O_2$ and a decrease in pH reduces the affinity such that $O_2$ is released at the cellular level. As the blood in the lungs has a higher pH than blood in the tissues (by virtue of the lower $CO_2$ concentration) the pH dependence of haemoglobin affinity allows $O_2$ to be collected in the lungs and transported for delivery to the tissues at the lower pH.

It will be appreciated therefore that if the pH of blood in the tissues increases, the affinity of haemoglobin for $O_2$ will increase, thereby reducing $O_2$ availability to the cells. pH is related to the partial pressure of $CO_2$ in the arterial blood ($PCO_2$). An optimum $PCO_2$ is required for optimum delivery of $CO_2$ to the cells.

Changes in blood pH can also lead to major metabolic problems.

Ventilation is primarily controlled by $PCO_2$ and ventilation will cease when $PCO_2$ falls below a point known as the apneic threshold. $PCO_2$ is actively regulated to remain constant. The $PCO_2$ homeostatic set point for a normal person is about 40 mm Hg that is well above the apneic threshold of about 32 mm Hg.

During exercise, more $CO_2$ is generated such that the $PCO_2$ raises above the homeostatic set point of about 40 mm Hg. This has the effect of increasing ventilation rate such that more $CO_2$ is excreted. Generally, there is a close match between $CO_2$ produced and excreted such that the $PCO_2$ remains at about 40 mm Hg. This also maintains blood pH at about 7.3 that ensures proper oxygen supply to the cells. To further assist in circulation and enhance oxygen and glucose transfer to the muscles, blood vessel diameter increases with higher $PCO_2$. Conversely as $PCO_2$ drops, the blood vessels contract.

Matching metabolic $CO_2$ generation with $CO_2$ excretion is therefore very important. Unlike most other homeostasis mechanisms in the body, such as control of body temperature, ventilation can be voluntarily controlled to some extent. If a person holds their breath, metabolic $CO_2$ increases to a level that ventilation can no longer be voluntarily controlled and a person eventually has to breathe.

On the other hand, if a person breathes out more $CO_2$ than is produced, $PCO_2$ falls, blood pH increases, thereby increasing the affinity of haemoglobin for $O_2$ and reducing its availability to the cells. This occurs during hyperventilation. People hyperventilate due to stress or just before physical exertion. In the latter, the blown off $CO_2$ is quickly replaced by metabolic $CO_2$ as a result of the exertion.

However, if the hyperventilative state continues for longer than several hours, the high pH triggers the acid base homeostatic mechanism in the body to decrease the pH to its normal level. The kidneys begin to retain acid and excrete alkaline bicarbonate buffer, which returns the pH to the normal value of 7.3. It will be appreciated that the plasma pH is now normal but with a lower $PCO_2$. As the blood concentration of bicarbonate buffer has been depleted, the person is much more sensitive to pH changes. Such a person is suffering from hyperventilation syndrome (HSV)

HVS is a recognised condition with serious side effects. It is relatively common but often undiagnosed. HSV does not appear to have any organic cause and many people with HSV suffer from various stress disorders that may have caused the original over breathing. Pharmacological intervention is often used for treatment of the underlying stress disorder together with breathing exercises and behavioural therapy.

For a person suffering from HSV, if $PCO_2$ is increased such as during exercise, in the absence of a normal blood buffering capacity, the $PCO_2$ increase will quickly increase blood acidity. If the residual buffer cannot compensate for the increase in acid, the respiratory centre is stimulated to help regulate the body fluid pH by increasing ventilation rate and eliminating $CO_2$. Such people are frequently out of breath and are intolerant to exercise.

Whilst not wishing to be bound by theory, it is believed that such a circumstance serves to reset the homeostatic set point such that the breathing reflex will be stimulated when $PCO_2$ is in the order of 36 to 39 mm Hg that is below the normal $PCO_2$ of about 40 mm Hg.

Turning now to DSA's as discussed above, they operate by mandibular advancement and/or bringing the tongue forward so as to open the airways so as to increase the airflow into the lungs. This appears to be a logical solution and is the well established understanding of those of skill in the art of DSA's. Many MADs not only allow mouth breathing but actively encourage mouth breathing.

The present inventor has appreciated that such an approach not only fails to take into account the physiological and biochemical feedback mechanisms that control ventilation as discussed above, but actually makes the condition worse.

The present inventor has appreciated that not all of the air in each breath is available for $O_2$ and $CO_2$ gas exchange as a result of the dead space in the lungs, nose and throat. Dead space volume is an important buffer between arterial $CO_2$ and the atmospheric $CO_2$ which has very low levels of $CO_2$. Without the dead space, the $PCO_2$ would quickly fall below the apneic threshold.

When a person breathes through the mouth, the dead space volume decreases as the nasal passages are no longer part of the ventilation route. This allows more $CO_2$ to be lost such that there becomes an imbalance between metabolic $CO_2$ and exhaled $CO_2$. This loss of $CO_2$ raises the pH. Continual mouth breathing will raise the pH to levels at which the kidneys are engaged to return the pH to normal values as described above.

The present inventor believes that for this reason, the homeostatic set point for habitual mouth breathers may be reset such that ventilation is stimulated at $PCO_2$ levels below 40 mm Hg as described above.

The present inventor has recognised that mouth breathers may suffer from many of the symptoms and complications of HVS. This link between mouth breathing and homeostatic set point has not been recognised by those of skill in the art of DSA's. This is clear from the fact that the major types of DSA may exacerbate symptoms of SDB such as chronic tiredness and fatigue. A person may stop snoring due to the physical movement of the tongue away from the airway but the person will still be tired.

For example, DSA's of the MAD type that open up the airway and encourage unrestricted mouth breathing, although increases $O_2$ intake allows more metabolic $CO_2$ to be excreted. As discussed above, this increases blood pH and reduces oxygen that is available to the cells. A person may feel short of breath despite having sufficient oxygen in the blood stream. This clearly contraindicates to a good night's rest. Such people will still be tired upon waking.

In mouth breathing (and other oral myofunctional disorders) the relevant muscles of the face and mouth have been programmed to help a person breathe in a dysfunctional manner. When the devices are removed, the person simply reverts immediately to mouth breathing.

Currently, the only way to actually stop mouth breathing is through myofunctional therapy so as to retrain the muscles to function in new ways. Myofunctional therapy includes facial and tongue exercises and behavior modification techniques to promote proper tongue position, improved breathing, chewing, and swallowing. Myofunctional therapy requires strict compliance with the exercises set by the myofunctional therapist and regular therapeutic sessions. Not all patients, and in particular children, are compliant.

Forcing mouth breathers to nasal breath in their sleep by completely blocking the mouth has been proposed. The simplest approach merely tapes the mouth together. Chin straps that prevent the mouth from opening are also well known. Tongue retaining devices that extend the tongue forward between the lips also prevents or significantly reduces mouth breathing. However, such an abrupt solution plays no part in retraining breathing habits.

These devices that do not permit mouth breathing and force nasal breathing are equally as ineffective and disadvantageous in treating snoring and SDB as MADs but for a different reason. Taping the mouth or inserting a device that prevents mouth breathing may appear to address the problem of snoring caused by mouth breathing. Superficially, this may appear to be not only a viable solution but also advantageous given the known benefits of nasal breathing such as providing moist, filtered air to the lungs and avoiding a dry mouth.

However, as discussed above, the present inventor has recognised that habitual mouth breathers may have their homeostatic set point to stimulate ventilation at $PCO_2$ levels below the normal level of about 40 mm Hg and insufficient blood buffering capacity. Forced nasal breathing will suddenly increase the dead space volume and suddenly increase $PCO_2$ This will quickly lower the blood pH and the respiratory system will be stimulated to increase ventilation rate i.e. to hyperventilate so as to "blow off" excess $CO_2$, which the body would normally do to exhale excess metabolic $CO_2$ during exercise. In other words, the person will over breath, to keep $PCO_2$ at below normal levels which in turn is associated with higher pH and lower oxygen availability. When the device is removed during the day, the person will revert to mouth breathing, which will maintain a normal blood pH.

The disclosed method acts first by regulating and controlling the volume of air that is inhaled and exhaled through the mouth by means of the breathing holes in the appliances. The first appliance has a cross sectional area for breathing that is reduced when compared to the cross sectional area for breathing without the appliance. This reduces the volume of air that is exchanged with each breath, thereby decreasing the amount of $CO_2$ that is exhaled allowing metabolic $PCO_2$ to increase. This lowers the pH, thereby allowing more oxygen to be released to the cells.

Whilst not wishing to be bound by theory, it is believed that this gradual step wise increase in $CO_2$ levels may reset the homeostatic set point so as eventually restore a normal breathing pattern, normal $PCO_2$ and buffering capacity of the blood.

As discussed above habitual mouth breathers may have a homeostatic set point that has been reset to stimulate ventilation at a lower value, such that such a person has a lower $PCO_2$ than normal. As a result of the kidneys excreting bicarbonate buffer, the buffering capability of the blood has been reduced and is less able to tolerate pH change than for normal blood having a normal bicarbonate content.

If a lowered $PCO_2$ level approaches the apneic level, the person will pause breathing for a period of time of breathing will become overly shallow. Both events results in an increase in $CO_2$ to increase to a level where ventilation is stimulated and the person will arouse or wake as breathing recommences.

An apneic event is defined where there is a pause in breathing for at least ten seconds. A hypopneic event is associated with a decrease in oxygen levels by 3 or 4 percent or an arousal or awakening from sleep.

By providing a relatively small decrease in the volume of air available for exchange with atmospheric air, metabolic $CO_2$ rises and triggers a series of physiological and biochemical responses. First, the relatively small increase in $PCO_2$ and subsequent small increase in acid favours available oxygen to the cells. It is believed that, this small increase may not significantly exceed the limited blood buffering capacity such that the pH does not lower sufficiently to significantly stimulate increased ventilation that will blow off more $CO_2$. A small increase in $PCO_2$ also slightly raises the levels of bicarbonate buffer that can accommodate further increases in $PCO_2$. Because the pH change is subtle, the kidneys are not stimulated to excrete bicarbonate.

That such a complex biochemical and physiological response can be initiated by the disclosed functional oral appliance and methods has never been contemplated in the art and is indeed a surprising result. Functional oral appliances as used in the myofunctional arts of correcting malocclusions and in the sleep disorder breathing art are designed for pure physical manipulation of the dentition and orofacial musculature.

Whilst not wishing to be bound by theory, the present inventor believes that the step wise reduction in breathing holes of the appliance used in each treatment step, slowly allows and encourages the patient to start breathing through the nose. This stepwise manner also assists in retraining and strengthening the orofacial muscles such as the lip muscles that keep the mouth closed.

The upper and lower dental arch receiving channels of the first and/or second oral appliance may be configured so that when the appliance is worn in the mouth, the patient's mandible is advanced. This brings the tongue forward and may alleviate any obstruction of the pharyngeal airway. The degree of mandibular displacement, if present, may suitable decrease from the first to the second oral appliance. In some methods, the final stage oral appliance may have no mandibular displacement.

Suitably, the degree of advancement is significantly less than conventional MAD's that advance the mandible 50% to 75% of the maximum degree of protection of about 7 mm to about 12 mm. The purpose of this extent of advancement is to increase the oropharyngeal airspace and increase the overall airflow.

The degree of mandibular advancement in the first stage appliance is suitably less than 5 mm that is the minimum recommended by the AADSM and is most suitably between about 1 to about 3 mm. This brings the tongue forward sufficiently such that the tongue does not block the airway. The aim of the present appliances is to control air flow not maximise air flow. As described above, maximising unrestricted airflow has adverse effects on a patient's breathing pattern.

In further embodiments, any one or more of the stages of treatment may further include wearing the oral appliance whilst awake. This may enhance the effect of regulating breathing and training the transition. Suitable times for wearing the appliance during the day or evening when the patient is awake is between about 20 minutes to about four hours, suitably between about one to about three hours, more suitably between about one to about two hours. It will be appreciated that wearing an appliance for the treatment of SDB whilst a patient is awake would appear to a person in light of the current SDB appliance treatment therapies to be illogical and ineffective. In fact, that a person does not wear a conventional MAD during the day is considered desirable so as to reduce side effects and to provide relief to the TMJ. Many MAD patients report TMJ soreness in the mornings and a noticeable change in bite.

The present inventor has also observed that mouth breathing in children can have significant and serious consequences on facial growth alterations and/or orofacial muscle tone that can predispose a child and the eventual adult to SDB.

It may be appreciated that there are considerable adverse health effects that are caused by mouth breathers who may not yet exhibit SDB symptoms. It is therefore desirable to be able to train a mouth breather, who does not exhibit SBD symptoms, to change their breathing pattern from oral to nasal.

The present disclosure therefore also relates to a method of training a person to breath primarily through their nose, the method comprising the steps of;

(a) providing a set of oral appliances comprising a first and at least a second oral appliance, wherein each of the first and at least second oral appliances comprises;

a generally U shaped appliance body with a front and two arms, the appliance body including an inner wall and an outer wall;

a web interconnecting the inner wall and the outer wall, the web having a front section and two arms with trailing ends;

each of the inner wall and outer wall have an upper portion that projects above the web so as to define an upper dental arch receiving channel;

each of the inner wall and the outer wall have a lower portion that depends from the web so as to define a lower dental arch receiving channel; and cross sectional area for breathing and the total cross sectional area for breathing of the first appliance is larger than the total cross sectional area for breathing of the second oral appliance;

(b) causing the patient to wear the first oral appliance in a first treatment stage whilst sleeping for a first period of time; and (c) causing the patient to wear the second oral appliance in a second treatment stage whilst sleeping for a second period of time.

If SBD symptoms have appeared such as the tongue partially blocking the pharyngeal airway during sleep upper and lower dental arch receiving channels of the first and/or second oral appliance may be configured so that when the appliance is worn in the mouth, the patient's mandible advanced. This brings the tongue forward and may alleviate any obstruction of the pharyngeal airway. The degree of mandibular displacement, if present, may suitable decrease from the first to the second oral appliance. In some methods, the final stage oral appliance may have no mandibular displacement.

If SBD symptoms have not yet occurred, it may not be necessary for any appliances in the set for use in the above method to advance the mandible.

All the appliances for use in the above methods include a web interconnecting the inner wall and the outer wall which is positioned between the dentition on the upper and the lower arches when the oral appliance is fitted within the patient's mouth. Thus the web lies broadly in the occlusal plane between the dentition of the upper and the lower arches in use.

The web of at least the first appliance is suitably dimensioned so as to prevent the lips from closing over the breathing holes. In the first and second stage appliances. This is important for ensuring the control of the volume of air that is being breathed through the mouth. The web dimensions may decrease with subsequent appliances as the patient is trained towards nasal breathing. In the final stage appliance, the web may be dimensioned such that the patient may be able to close their lips over the breathing holes. This allows the patient to have some control in the final stages of treatment. In these final stages, the patient's $PCO_2$ and buffering capacity will be approaching normal levels, the orofacial muscles will have been retrained for nasal breathing and the patient will proceed to close the lips when over the final stage appliance and fully mouth breathe. When the appliance is removed, the patient will continue to nasal breathe.

The web suitably thickens from the front of the web to a point towards the trailing ends of the arms. This tends to fill in the space between the teeth of the upper and lower jaw. This in some respects resembles an airfoil and thickens the web. This arrangement puts more pressure on the rear molars thereby relaxing and exercising the joints and muscles.

Suitably, the thickened portions of the web are compressible. Compression may be achieved by providing a section of softer or more compressible material. Suitably compression is achieved by providing one or more holes through the trailing ends of the arms of the web.

The combination of the airfoil shape and the ability to compress that part of the web between the rear molars can alleviate TMJ pain and other discomfort that is felt by users of conventional rigid devices. For example many prior art MAD devices of the mouth guard type are similar to mouth guards of the boil and bite type. These are well known and are formed of a heat deformable plastic such as ethylene vinyl acetate in which the guards are user molded to the shape of a user's teeth and arch.

Further still the ability to compress the web allows movement of the users jaws relative to each other, further alleviating discomfort and more importantly by allowing such movement allows for oral muscle retraining and development.

The compressible hole may also serve a double function as a breathing hole.

The inner wall of the appliance includes an upper portion which projects above the web and a lower portion which depends from the web, when the appliance is fitted in the patient's mouth.

The inner wall may have two major surfaces, namely a lingual surface which faces inward towards the tongue, and a channel surface which faces outward into the arch receiving channels.

The outer wall may also have two major surfaces, namely a buccal surface which faces outward towards the buccal mucosa, and a channel surface which faces into the arch receiving channels.

Suitably, the inner and outer walls are dimensioned such that may be retained within the oral cavity when the patient is asleep with the mouth open.

As the walls define upper and lower channels for receiving a dental arch, the inner and outer walls include a front portion and two arm portions extending away from the front portion.

The front portion of the inner wall may incline rearward away from the outer wall as it extends up from the web. This angle of inclination is suitably selected to adopt the natural curvature of the palate so as to provide comfort when wearing the appliance.

The appliance may include a tongue tag formed in the upper portion of the inner wall, e.g. substantially centrally on the inner wall, or substantially midway along the inner wall, corresponding to the midline of the patient's dentition.

The inner wall may form a circumferential edge around the tongue tag and the circumferential edge may be rounded. In particular the circumferential edge may be rounded where the tongue opening transitions from a position inside the opening onto the lingual and channel surfaces of the inner wall.

The tongue tag may serve as an indicator for the correct positioning of the tongue in a forward position to enlarge a restricted airway. The tongue tag will be discussed further below.

The appliance body may be formed from a polymeric material. In particular the appliance body is formed from a polymeric material that is polyurethane or silicone, e.g. by injection moulding.

Silicone is particularly suitable as it is pliable and does not require moulding to a user's teeth. This may improve comfort; allow the user some jaw movement that will also contribute to user comfort and thus compliance.

The appliance body may be made in a number of different sizes and the sizes may be selected so that a majority of the population can select an appliance that can be fitted over their upper arch with a reasonable fit. Typically there may be three to four different sizes of the appliance body.

The method uses a set of two or more appliances with a staged reduction on cross sectional area for breathing. The breathing holes are in the web of the appliance. The first stage appliance may have 2-4 relatively large breathing holes at the front. One or more breathing holes may also be located towards the rear of the web.

In addition to allowing breathing, the air holes provide a degree of flex that allows gentle compression of the jaw joints.

The second appliance suitably has a similar number of holes. Alternatively, the number of holes may be reduced.

Suitably for both methods as disclosed above, the methods further include providing at least a third oral appliance, wherein the further appliance(s) are for use in further stages of treatment and in each stage of treatment the cross sectional area available for breathing is reduced.

Suitably the treatments are in 3 to 6 stages with 3 to 6 appliances, each appliance with reducing air breathing cross sectional area.

Thus with successive appliances, less overall volume of air is inhaled. A final stage appliance may have one or two holes with a width or diameter of 1 mm or less. In some methods, the last stage appliance may have no breathing holes at all.

In some aspects of either of the above methods, the thickness of the web may decrease with successive appliances. The thickness of the web to some extent determines how far the jaws are held apart by the appliance. Decreasing the thickness of the web, allows for the jaws to get closer over the treatment regime towards being fully closed for nasal breathing.

The upper and lower arch receiving channels may be configured so that when worn, the mandible is advanced. In some embodiments, the methods may use appliances in which the degree of mandibular advancement decreases together with the total cross sectional area for breathing.

Where a tongue tag is present and the tongue is positioned on the tongue tag which may counter the retractive action of the appliance on the upper jaw. In some cases, this may advance the upper jaw.

Suitably at least the first stage appliance has a tongue tag with a diaphragm like characteristic, to initially "suck" the tongue tip upwards and forwards to enlarge the restricted airway The diaphragm tongue tag may progressively get thinner with each stage of appliance and in some embodiments may eventually become a hole for receiving the tip of the tongue.

As a result of the combined action of the mandibular advancement and bringing the tongue forward, less mandibular advancement may be required with the appliances and methods herein disclosed than with conventional MAD appliances. This may reduce the side effects and allow the presently disclosed appliances to be safely used on adults and children.

The stages of treatment may depend upon a number of factors such as the age of the patient, the degree of mouth breathing and the severity of the SDB. The appliances should be worn in the mouth.

Suitably, the stages may vary between 1 to 3 months. The total treatment may be up to one to two years. Progress of treatment may be monitored by a health professional. Known methods of monitoring SDB include measuring the apnea-hypopnea index, or AHI. AHI is an index used to assess the severity of sleep apnea based on the total number of complete cessations (apnea) and partial obstructions (hypopnea) of breathing occurring per hour of sleep; blood oxygen saturation and assessing day time sleepiness However, in view of the current novel approaches herein disclosed, it is believed to be more suitable to measure a patient's $PCO_2$ prior to commencing treatment and to monitor $PCO_2$ during treatment and the next stage of treatment commences when a predetermined $PCO_2$ has been obtained.

Any suitable method of measuring $PCO_2$ may be employed. One method of assessing $PCO_2$ is by capnography that reads the level of $CO_2$ in expired air (end-tidal $CO_2$) by infra-red spectroscopy. Another method is transcutaneous monitoring that is done by an infrared transducer applied to the skin.

In some cases, a patient and/or practitioner may not have access to the equipment required for such measurement. The time that a person can hold their breath has been proposed as an indirect measure of $PCO_2$. The breathing holding time (BHT) technique measures in seconds the time a person can comfortably hold their breath after exhalation.

Persons with breathing disorders generally have a BHT of about 20 seconds or less. This generally correlates to a $PCO_2$ of about 30 mm Hg to 35 mm mm Hg or less. Those with a normal breathing pattern have a BHT of 60 seconds or longer, that generally correlates to a normal $PCO_2$ of about 40 mm Hg.

One possibility for such a correlation is that as discussed above the blood of a person with a breathing disorder often has a low blood buffering capacity. Holding one's breath allows metabolic $CO_2$ to increase. For a person with a low blood buffering capacity holding breath will cause a rapid decrease in pH that stimulates the respiratory center to breath.

Assessment of the $PCO_2$ prior to commencement of treatment provides a base line BHT and may also be used to assess the appliance breathing hole cross section that may be used in the first stage of treatment. For example, a person with a CP of 20 seconds or lower will most usually begin with an appliance having the largest holes, generally an appliance having four breathing holes that are 5 mm to 10 mm wide or, if circular, in diameter. A person with a BHT of 40 seconds may begin treatment with an appliance having smaller holes.

Suitably, BHT will be measured periodically after commencement of treatment. Within about one to three months an improvement in $PCO_2$ should be observed. Generally when the BHT has increased to between about 30 to about 40 seconds, the patient will begin using the second stage appliance.

The BHT will continue to be monitored and when it reaches about 40 to about 50 seconds, the patient will begin using the third stage appliance and continue to do so until BHT reaches about 60 seconds that is considered normal.

In further embodiments, any one or more of the stages of treatment may further include wearing the oral appliance whilst awake. This may enhance the effect of regulating breathing and training the transition. Suitable times for wearing the appliance when awake include between about 20 minutes to about four hours, suitably between about one to about three hours, more suitably between about one to about 2 hours.

In one aspect, at least one of the appliances is made from a flexible base material such as silicone and has one or more breathing holes at the front of the appliance that can be compressed when the user bites down onto the web, whereby the holes are configured such that it is not possible to fully close the breathing holes. Suitably, the or each hole is configured for a maximum compression that reduces the passive cross sectional area for breathing to a predetermined compressed cross sectional area for breathing. Suitably the compressed cross sectional area for breathing is no than about 80%, suitably by more than 70%, suitably by no more than 60%, suitably by no more than 50%, suitably by no more than 40% of the passive cross sectional area for breathing.

One suitable configuration of breathing hole may include two opposed and spaced apart projections extending from the upper and lower wall of the hole. As the hole is compressed such that the upper and lower hole walls are pushed together, the projections will eventually meet and prevent further compression. The person can continue to breathe through the spaces on either side of the abutted projections.

An advantage of this arrangement is that the holes cannot be fully closed so as to prevent the patient from breathing through their mouth. As explained above, a sudden increase in $PCO_2$ can stimulate hyperventilation.

Consciously compressing the holes and reducing the cross sectional area for breathing, can facilitate transition to the next stage appliance. Suitably the compressed cross sectional area is close to that of the next stage appliance.

The ability to bite down to compress the or each hole can also actively and consciously train nasal breathing.

The compressible nature of the holes allows a person to actively and consciously decrease the cross sectional area for breathing when they are wearing the appliance when awake. This would normally be done on the first stage device after about one to three months of treatment, when the patients $PCO_2$ has increased, as would be generally indicated by an increase in BHT.

Appliances in the further stages of treatment can similarly be provided with a hole or holes having a predetermined maximum degree of compression.

A person who normally nasal breathes with a closed mouth has lips that seal against each other easily with non-forceful movement. This requires the muscles of the lips and cheek to be efficient with normal muscle tone. On the other hand, the lips and cheeks of mouth breathers generally have poor muscle tone (hypotonic) that makes it difficult to make and maintain an efficient lip seal. An efficient lip seal is important for nasal breathing.

As discussed above, the width of the web that controls the bite reduces from the widest in the first stage appliance and the patient gradually moves the lips towards a closed position. Over the treatment period the muscles of the lips and cheeks are trained towards being able to form a lip seal, even when the patient is asleep.

Another disadvantage of mouth breathing, as discussed above, is that as the mandible drops, tongue position drops so as to allow the person to breathe through the mouth. Nasal breathing places the tongue in the correct position that is pressed against the roof of the mouth. This promotes suction that assists in an efficient mouth seal.

As discussed above in one embodiment, the disclosed appliance has a tongue tag for assistance in training a patient to correctly position their tongue.

Training of the tongue and lips as discussed above is essentially passive. Generally, as discussed above, the patient will also undergo myofunctional therapy to retrain the lips and tongue.

The patient is told to compress the compressible member with the lips, thereby improving competency of the lips. Suitably, the patient would compress the member for about 10 to about 60 seconds.

Also described herein is a set of oral appliances for use in a method of treating sleep disorder breathing in a patient, the set of oral appliances comprising a first oral appliance and at least a second oral appliance, wherein each of the first oral appliance and at least second oral appliance comprise;
  a generally U shaped appliance body with a front and two arms, the appliance body including an inner wall, an outer wall;
  a web interconnecting the inner wall and the outer wall, the web having a front section and two arms with trailing ends;
  each of the inner wall and outer wall have an upper portion that projects above the web so as to define an upper dental arch receiving channel;
  each of the inner wall and the outer wall have a lower portion that depends from the web so as to define a lower dental arch receiving channel; and
  wherein the web comprises at least one breathing hole so as to define a total cross sectional area for breathing and the total cross sectional area for breathing of the first oral appliance is larger than the total cross sectional area for breathing of the second oral appliance.

The upper and lower dental arch receiving channels of the first and/or second oral appliance may be configured so that when the appliance is worn in the mouth, the patient's mandible is advanced. This brings the tongue forward and may alleviate any obstruction of the pharyngeal airway. The degree of mandibular displacement, if present, may suitable decrease from the first to the second oral appliance. In some aspects, the final stage oral appliance may have no mandibular displacement.

Further disclosed is a set of oral appliances for use in training a person to breath primarily through their nose, the set of appliances comprising a first oral appliance and at least a second oral appliance, wherein each of the first and at least second appliance comprises;
  a generally U shaped appliance body with a front and two arms, the appliance body including an inner wall, an outer wall;
  a web interconnecting the inner wall and the outer wall, the web having a front section and two arms with trailing ends;
  each of the inner wall and outer wall have an upper portion that projects above the web so as to define an upper dental arch receiving channel;
  each of the inner wall and the outer wall have a lower portion that depends from the web so as to define a lower dental arch receiving channel; and
  wherein the web comprises at least one breathing hole so as to define a total cross sectional area for breathing and the total cross sectional area for breathing of the first oral appliance is larger than the total cross sectional area for breathing of the second oral appliance.

The upper and lower dental arch receiving channels of the first and/or second oral appliance may be configured so that when the appliance is worn in the mouth, the patient's mandible is advanced. This brings the tongue forward and may alleviate any obstruction of the pharyngeal airway. The degree of mandibular displacement, if present, may suitable decrease from the first oral appliance to the second oral appliance. In some aspects, the final stage oral appliance may have no mandibular displacement.

DETAILED DESCRIPTION

Figure 1:
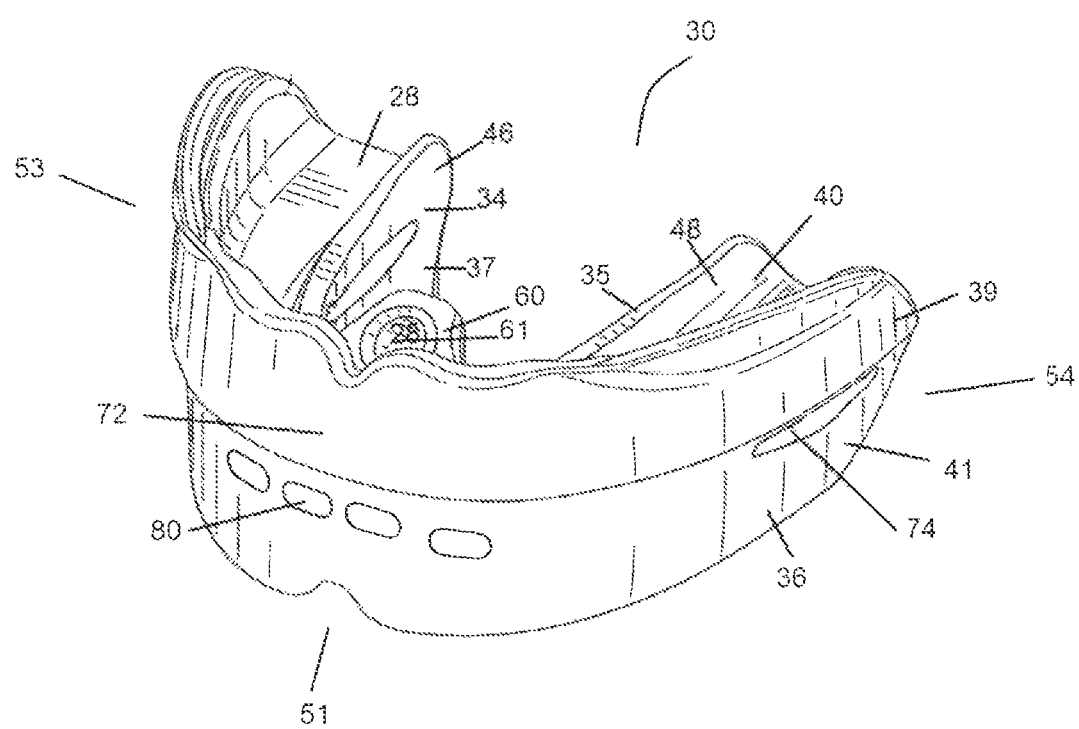
FIG. 1 is a top front perspective view of one aspect of a first stage oral appliance as disclosed herein.

An oral appliance and methods in accordance with this invention may manifest itself in a variety of forms. It will be convenient to hereinafter describe several embodiments of the invention in detail with reference to the accompanying drawings. The purpose of providing this detailed description is to instruct persons having an interest in the subject matter of the invention how to carry the invention into practical effect. However it is to be clearly understood that the specific nature of this detailed description does not supersede the generality of the preceding broad disclosure.

FIGS. 1 to 4 show perspective and front and rear views of an appliance 30 that is suitably a first stage appliance. The appliance 30 is made of medical grade silicone that is a rubber material that is flexible and comfortable in the mouth.

The appliance 30 includes an appliance body for mounting over the upper arch of a user. The appliance body includes an inner wall 34 that is positioned on a lingual side of the patient's upper arch and an outer wall 36 that is positioned on the buccal side thereof. The appliance body also includes a web 28 interconnecting the inner wall 34 and the outer wall 36. When the appliance 30 is in the mouth of a user, the web 28 lies in the occlusal plane between the dentition of the upper and the lower arches in use.

The inner and outer wall 34 and 36 and web 28 define upper and lower arch receiving channels 40 and 42 within which respectively the upper arch and associated dentition and the lower arch and associated dentition can be received.

The inner wall 34 includes an upper portion 35 which projects up from the web 28 and a lower portion 37 which projects down from the web 28. Similarly the outer wall 36 comprises an upper portion 39 above the web 28 and a lower portion 41 below the web 38. Further the inner wall 34 has a lingual surface 46 and a channel surface 48.

The outer wall 36 has a front buccal surface 72 that is dimensioned so that it substantially covers the buccal aspects of the upper and lower posterior teeth when the mouth is closed. In this way any force from overactive lip muscles can be dispersed over the surface 72 rather than applied to the teeth.

The inner wall 34 defines a tongue tag 60 for locating the tip of a patient's tongue. The tongue tag 60 is formed substantially centrally in the upper portion 35 of the inner wall 34 corresponding to the midline of the patient's dentition.

The inner 34 and outer 36 walls include a frontal portion 51 and two arm portions 53, 55 extending away from the frontal portion 51. The frontal portion 51 of the inner wall 34 inclines rearwardly away from the outer wall 36 as it extends up from the web 28 at an angle of about 30 to 40 degrees. In particular a region of the inner wall 34 within which the tongue tag 60 is formed may incline rearward at an angle of 30 to 40 degrees.

The tongue tag 60 has a circular thinned diaphragm section 61 that can move in and out in response to pressure exerted by the tongue. When the tip of the tongue presses on and deforms the diaphragm, a slight suction is produced that can assist in keeping the tip of the tongue on the tongue tag.

Figure 2:
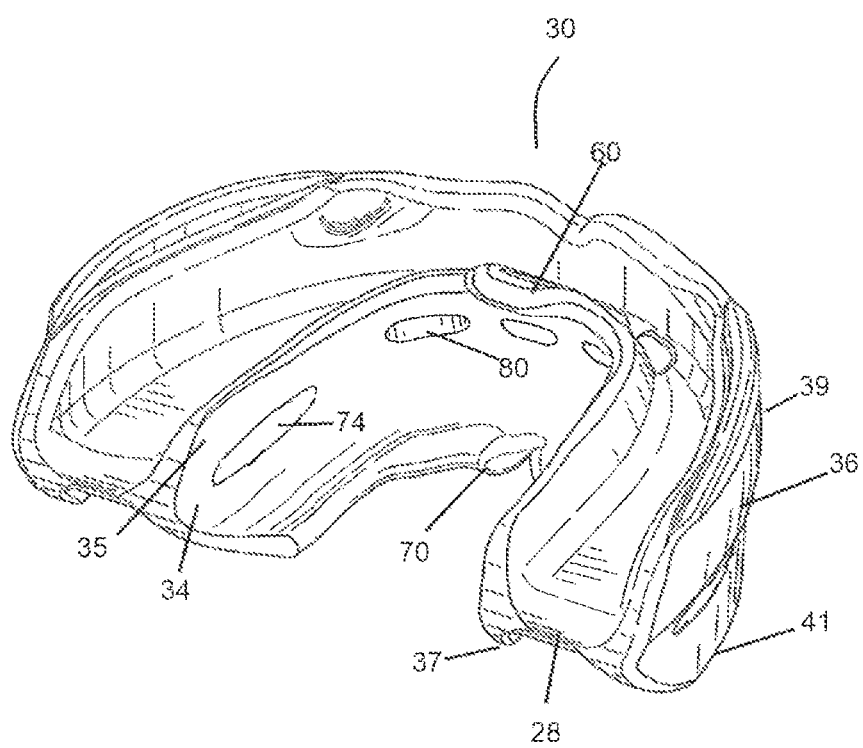
FIG. 2 is a rear top perspective view of the first stage oral appliance shown in FIG. 1.
Figure 3:
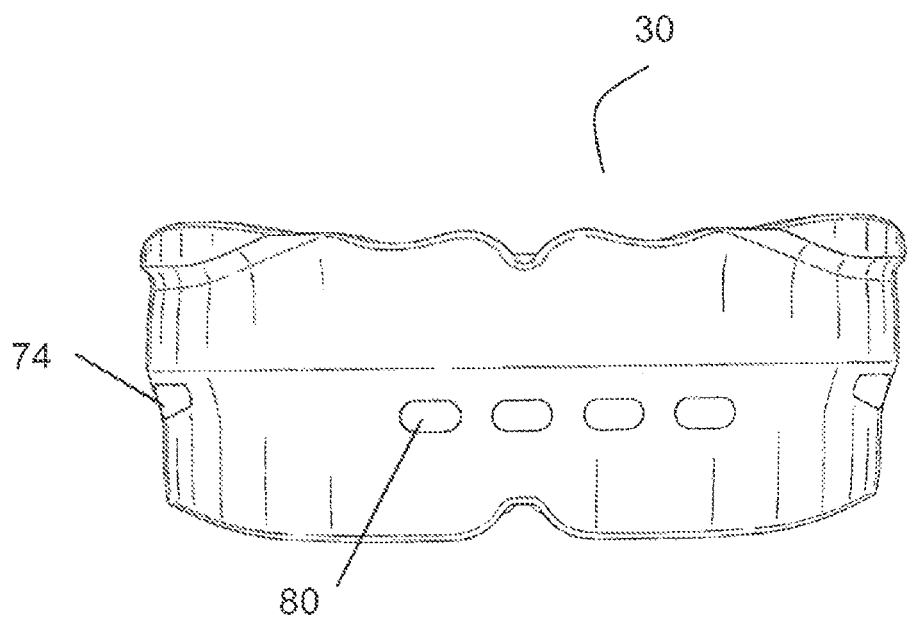
FIG. 3 is a front view of the first stage oral appliance shown in FIG. 1.
Figure 4:
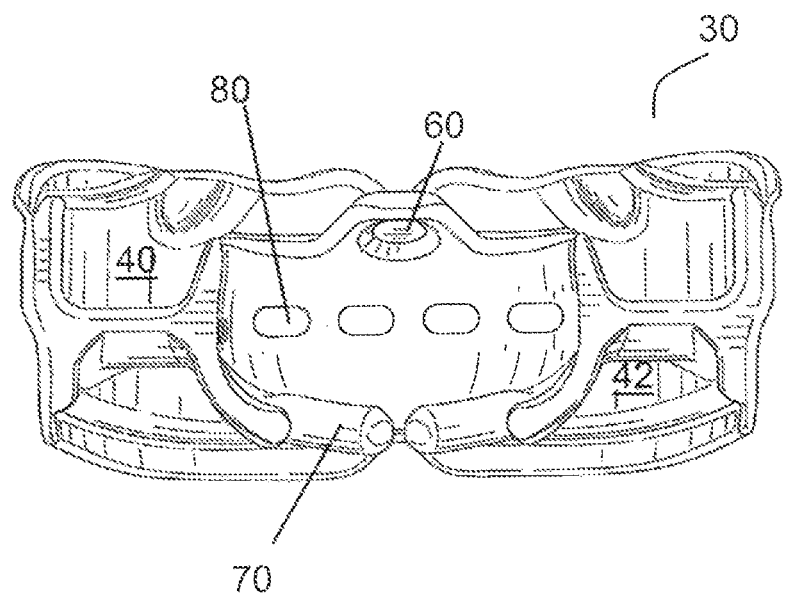
FIG. 4 is a rear view of the first stage oral appliance shown in FIG. 1.

The lower portion of the inner wall 34 includes a tongue elevator 70 (shown in FIGS. 2 and 4). The inner wall 34 has a lower terminal edge region 52 and the lower terminal edge region is thickened to form the tongue elevator 70. The tongue elevator 70 forces the tongue to hold an upwards position that assists in bringing the tongue forward so as to open the airway.

The frontal portion 51 has four equally spaced breathing holes 80 located therein Each arm of the web 28 also has a single hole 74 towards the trailing ends of the arms 53, 54. These holes will be discussed further below.

The hole(s) 74 in the arms of the web 28 not only assist in breathing but provide a degree of compression to that part of the web. This provides a degree of cushioning and resilience that not only provides comfort to the patient, but allows the patient to slightly move the teeth relative to each other. This can reduce the discomfort felt by wearing a rigid inflexible MAD device. Movement also allows exercise of orofacial muscles that is important in retraining the patient to nasal breathe.

Figure 5:
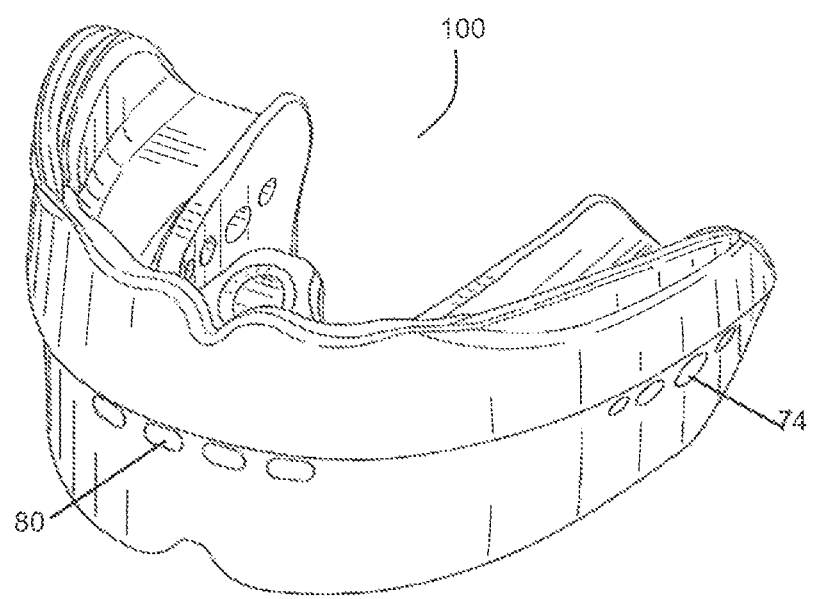
FIG. 5 is a front perspective view of a second stage oral appliance.
Figure 6:
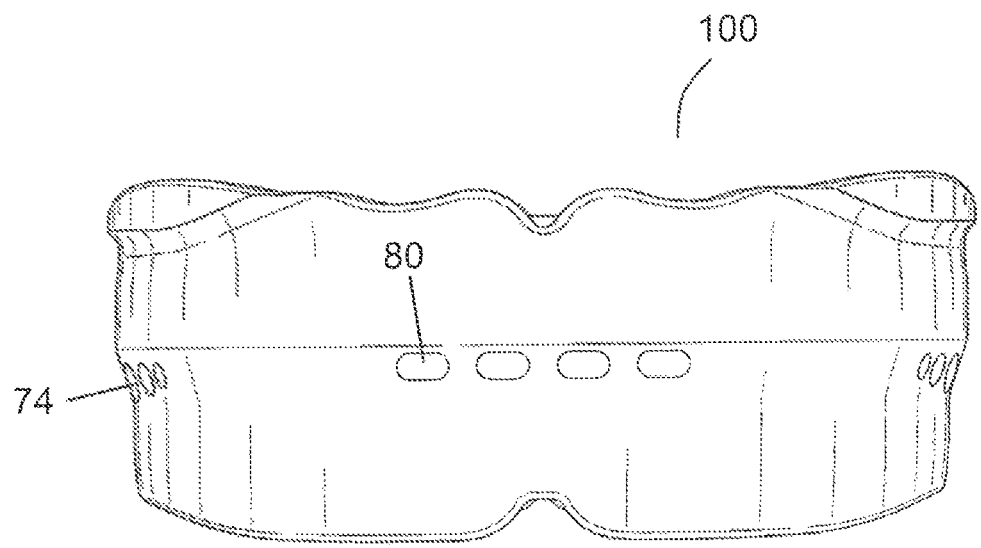
FIG. 6 is a front view of the second stage oral appliance shown in FIG. 5.
Figure 7:
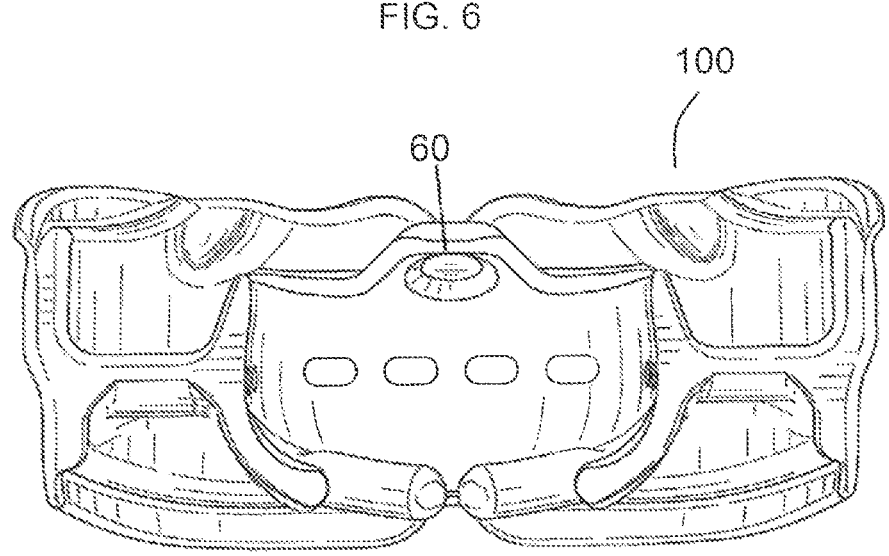
FIG. 7 is a rear view of the second stage oral appliance shown in FIG. 5.

FIGS. 5 to 7 show a second stage oral appliance 100. The same reference numerals will be used to describe the same features of the first stage appliance 30. In the second stage appliance the four holes 80 in the front thereof, have a total cross sectional area that is less than that of the first stage appliance It may be seen that instead of a single side hole, there is a series of four side holes 74 such that the cross sectional area for breathing of the side holes is less than that of the single side hole of the first stage appliance.

Figure 8:
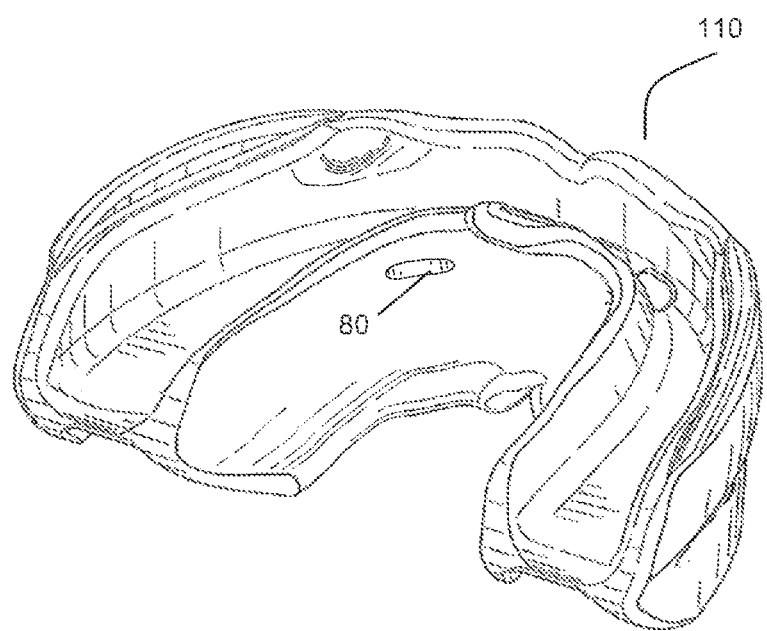
FIG. 8 is a rear perspective view of a third stage oral appliance.
Figure 9:
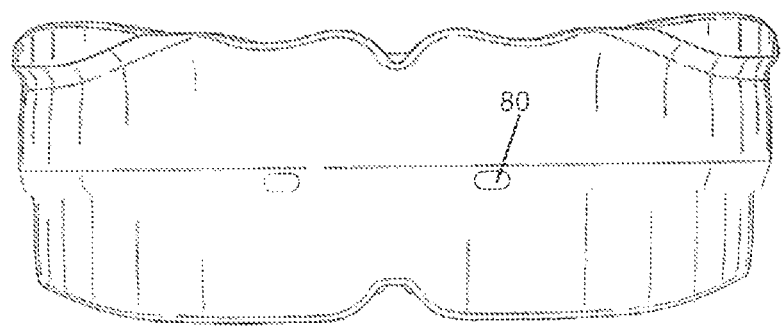
FIG. 9 is a front view of the third stage appliance shown in FIG. 8.
Figure 10:
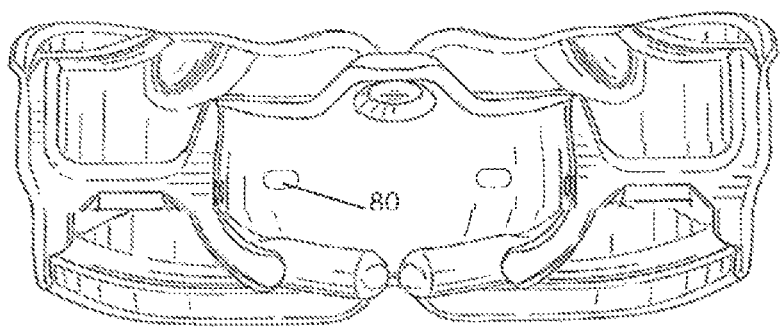
FIG. 10 is a rear view of the third stage appliance shown in FIG. 8.

FIGS. 8 to 10 show a third stage appliance 110 that has two small front breathing holes, thereby having a lower total cross sectional area for breathing through as compared to the first and second stage appliances the third stage appliance does not have any side holes.

Figure 11:
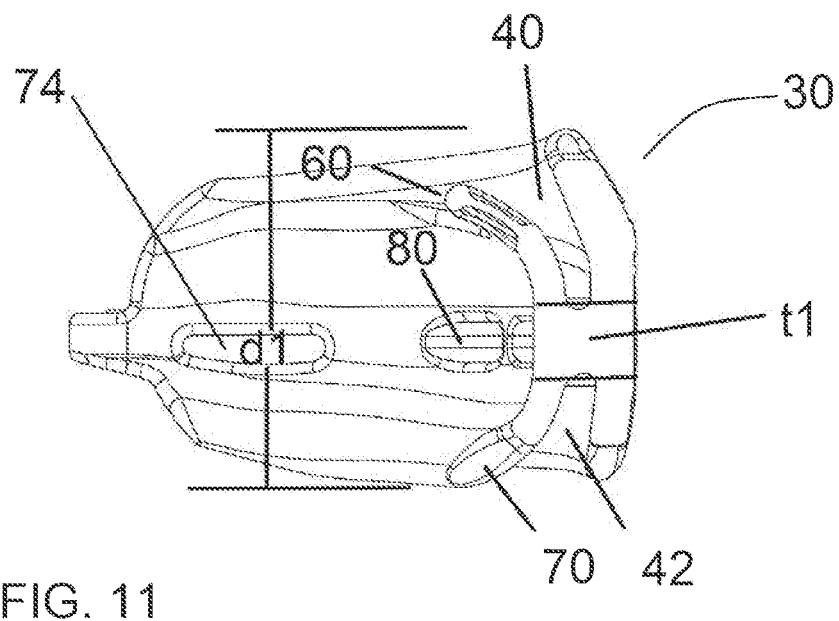
FIG. 11 is a cross section of the first stage appliance as shown in FIG. 1.
Figure 12:
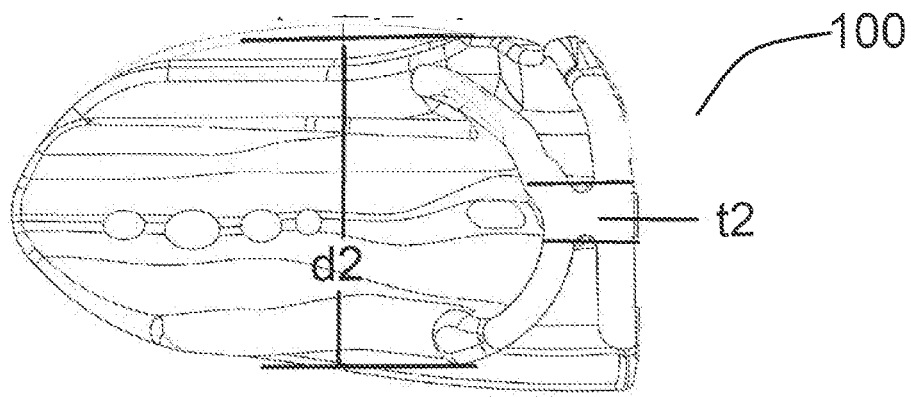
FIG. 12 is a cross section of the second stage appliance as shown in FIG. 5.
Figure 13:
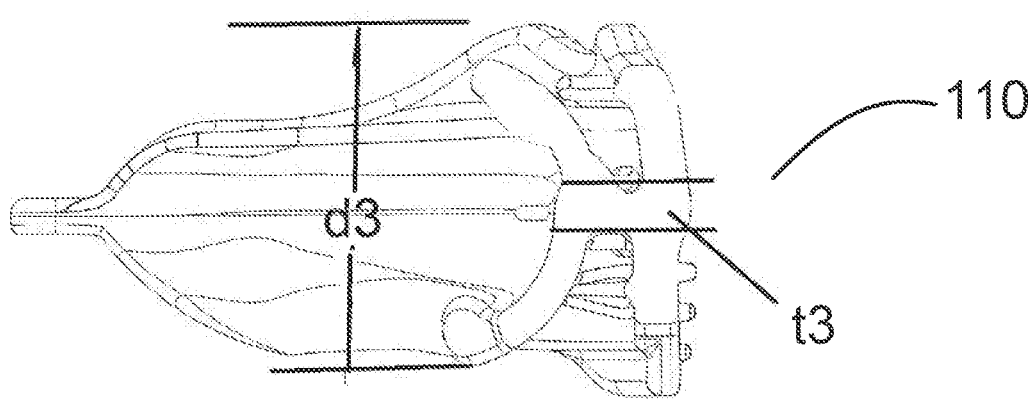
FIG. 13 is a cross section of the third stage appliance as shown in FIG. 8.

FIGS. 11, 12 and 13 are cross sections of the respective first stage 30, second stage 100 and third stage 110 appliances. These cross sections show further important differences between the appliances. These differences are (1) the thickness t1, t2, t3 of the web 28 at the front of the appliance;

(2) the relative alignment of the upper 40 and lower 42 dental arch receiving channels; (3) the respective overall depth of the appliances d1, d2, d3 and the distance between the tongue elevator 70 and the top of the upper dental arch receiving channel 40.

The thickness of the web 28 decreases from the first stage, through to the third stage appliance i e. t1>t2>t3. It will be appreciated that the thickness of the web 28 influences the openness of a patient's bite, or vertical dimension of opening. The first stage device typically has a web thickness t1 of about 3 mm to about 10 mm, typically between about 4 mm to about 6 mm. In one aspect t3 is about 5.5 mm. This thickness also accommodates the size of the four larger holes 80 that are typically between about 5 mm to about 10 mm in width.

The vertical dimension of opening is such that the patient cannot close their lips. It is important that the amount of air that is exchanged in one breath is controlled. If for some reason, the patient closes their mouth then the $PCO_2$ will rise significantly above the patient's reset homeostatic set point which will increase ventilation to expel further $CO_2$ This is clearly counterproductive as the eventual aim is to return $PCO_2$ to normal.

The second stage appliance 110 has a web thickness t2 that is smaller than t1 and is suitably between about 2 mm to about 5, typically between about 2.5 to about 3.5 mm. In one aspect, t2 is about 3 mm. This thickness is consistent with the decrease in size of the breathing holes. As discussed below, at this stage a patient will be starting to partially nasal breath.

The third stage appliance 110 has a minimal web 28 thickness t3 of between about 1 mm to about 4 mm, typically between about 2 mm to about 3 mm. In one aspect t3 is about 2.5 mm. This thickness allows the patient to close their lips and fully nasal breathe. The two small holes 80 allow minimal mouth breathing if the lips are not closed. As the patient begins to nasal breath further, closure of the lips will become patient controlled.

The second physical parameter of the respective appliances is the relative alignment of the upper 40 and lower 42 dental receiving arches. This alignment determines the degree of mandibular displacement, if at all.

The upper 40 and lower 42 arch receiving channels of the first stage appliance 30 are essentially in alignment. This provides for mandibular advancement of about 1 mm to about 3 mm. The second stage appliance 100 has a lesser degree of mandibular advancement of about 2 mm or less.

The third stage appliance allows for normal occlusion.

The third difference is the depth of the appliance and the distance between the tongue elevator 70 and the top of the upper dental arch receiving channel 40. As discussed above, correct forward positioning of the tongue is important for nasal breathing and proper facial musculature. The tongue elevator 70 raises the tongue slightly towards the more desirable position. When transitioning from the first 30 through to the third appliance 110, the position of the tongue is moved upwards towards the maxilla. This can assist in expanding the maxilla, with a concomitant increase in nasal passage size.

The distance d1 in the first stage appliance 30 is generally between about 25 mm and about 35 mm, typically between about 27 mm and about 32 mm. In one aspect d1 is about 30.8 mm.

The distance d2 in the second stage appliance 100 is generally between about 21 to about 31 mm, typically between about 23 mm to about 28 mm. In one aspect d2 is about 26.7 mm.

The distance d3 in the third stage appliance 110 like generally between about 19 mm to about 29 mm, typically between about 21 mm to about 26 mm. In one aspect d3 is about 25 mm.

The three different stage appliances may be used in a method for treating SDB in a patient.

Such a patient will generally show symptoms similar to that of HVS. The patient's $PCO_2$ will generally be below normal, the level of bicarbonate buffer in the blood will be depleted, thereby making the patient more sensitive to a change in pH caused by an increase in $PCO_2$. The blood pH will be higher than normal, thereby favouring the affinity of haemoglobin for $O_2$ and the patient is tired, despite a night's sleep.

Prior to treatment, $PCO_2$ will be evaluated, typically by the use of CP, although other known methods of evaluating $PCO_2$ may be used. A typical patient would generally have a CP of about 20 seconds or less. This generally correlates to a $PCO_2$ of about 30 mm Hg to 35 mm Hg or less.

The patient begins to wear the first stage appliance nightly and suitably for a period during the day for about 1 to 2 hours. Wearing of the first stage appliance and breathing through the holes in the appliance reduces the volume of air that is exchanged in each breath. This reduces the amount of metabolic $CO_2$ that is exhaled, thereby allowing metabolic $CO_2$ levels and $PCO_2$ to increase.

$PCO_2$ levels therefore rise, in a manner that is controlled by the cross sectional area of the breathing holes. By providing a relatively small decrease in the volume of air available for exchange with atmospheric air as compared to unrestricted mouth breathing, metabolic $CO_2$ rises and triggers a series of physiological and biochemical responses in a specific manner.

First, the relatively small increase in $PCO_2$ and subsequent small increase in carbonic acid levels lowers blood pH that favours available oxygen to the cells. A small increase in $PCO_2$ also slightly raises the levels of bicarbonate buffer that can accommodate further increases in $PCO_2$. It will be appreciated that the $PCO_2$ will be within or just above the lowered homeostatic set point such that the bodies' homeostasis response will not be or if so not significantly stimulated to increase ventilation so as to eliminate $CO_2$.

The patient should begin to feel more refreshed after a night's sleep as a result of an increase in $O_2$ availability to the cells.

With a gradual increase in $PCO_2$ that does not significantly reduce pH so as to stimulate hyperventilation, bicarbonate buffer levels rise, thereby allowing the body to tolerate increasing $PCO_2$ towards normal levels without simulating ventilation.

$PCO_2$ is monitored during this time, suitably by measuring PC. As the body is able to tolerate more $CO_2$, the person can hold their breath longer despite the increase in metabolic $CO_2$ and CP rises.

A further effect of the first stage appliance is physical in there is a limited degree of mandibular advancement of about 2-3 mm or less. This advancement is significantly less than art known MAD devices that extend the mandible to between about 7 mm and about 12 mm.

Mandibular advancement for a person having a normal bite will put some strain on the TMJ. The flexibility of the silicone material allows some relative movement of the mandible that may at least partially alleviate such strain. However, this strain is significantly less than the art known MAD devices. Common side effects of art known MAD devices include TMJ discomfort or pain and myofascial pain. Long term advancement can cause TMJ damage and dysfunction.

It is known that mandibular advancement causes a reciprocal retraction of the maxilla. As the lateral walls of the nasal cavity are mainly defined by the maxilla, retraction of the maxilla can reduce the size of the nasal cavity, thereby reducing tendency to nose breath and exacerbate the breathing disorder.

The present appliances include a tongue tag that trains the tongue in the correct forward position in which the tip is adjacent the anterior palate. This forward position may reciprocate any retractive forces on the maxilla that is caused by the mandibular advancement. Forward tongue position also opens the pharyngeal airway.

The combination of forward tongue position and minimal mandibular advancement of the present appliances allows opening of the pharyngeal airway to extents comparable with known art MADs that significantly advance the mandible. Thus there is less strain on the TMJ with use of the present appliances than with art known MADs. This allows for more patient comfort which generally translates to higher patient compliance. This location of the tongue also reciprocates retrusive action of the maxilla.

Further any snoring may be less due to the opening of the pharyngeal airways by the combined mandibular advancement and placement of the tongue.

Through the first treatment stage, the patient should be beginning to train the tongue to the correct physiological position, the homeostasis systems can tolerate gradually increasing $PCO_2$ and the patient should start to breathe more through their nose, thereby increasing air volume dead space that decreases metabolic $CO_2$ elimination and further increasing $PCO_2$ towards a normal level.

The Patient's $PCO_2$ will be monitored throughout this time, suitably by CP as discussed above. When the patient's BHT reaches between about 30 to about 40 seconds, the patient may advance to the second stage appliance.

In the second treatment stage, the second stage appliance will be worn by a patient every night for a further period of about 1 to 4 months and for a period of 1 to 2 hours during the day. As a result of further reduced air being inhaled through the mouth, the patient will be required to breathe more through their nose with a further decrease in the $CO_2$ level in the exhaled air. Buffer levels will continue to increase towards normal levels, the body can tolerate more $CO_2$ and the associated pH favourable for cellular $O_2$ delivery.

The patient's BHT will be monitored and when it reaches between about 40 and about 50 seconds, the third treatment stage will commence in which the patient wears the third stage appliance overnight and for period during the day. As a result of even further reduced air being inhaled through the mouth, the patient will be required to breathe even more through their nose with a further change in the $CO_2$ level in the exhaled air. The patient will be beginning to feel the benefits of better oxygen supply to the body and beginning to approach a normal breathing pattern rather than hyperventilation. The buffering capacity of the blood should be approaching normal. Snoring should be noticeably reduced or absent.

The TMJ position is in the normal unstrained position.

Third stage treatment will generally last for about 1 to about 4 months. CP is regularly monitored and when CP reaches a level of about 60 seconds, treatment may be withdrawn.

After the final stage the patient's breathing mode should be retrained so that the patient can nose breathe without any appliance. During sleep, the tongue is in the forward position and will not fall back to obstruct the airway. The patient will no longer be required to wear a CPAP or a DSA.

Figure 14:
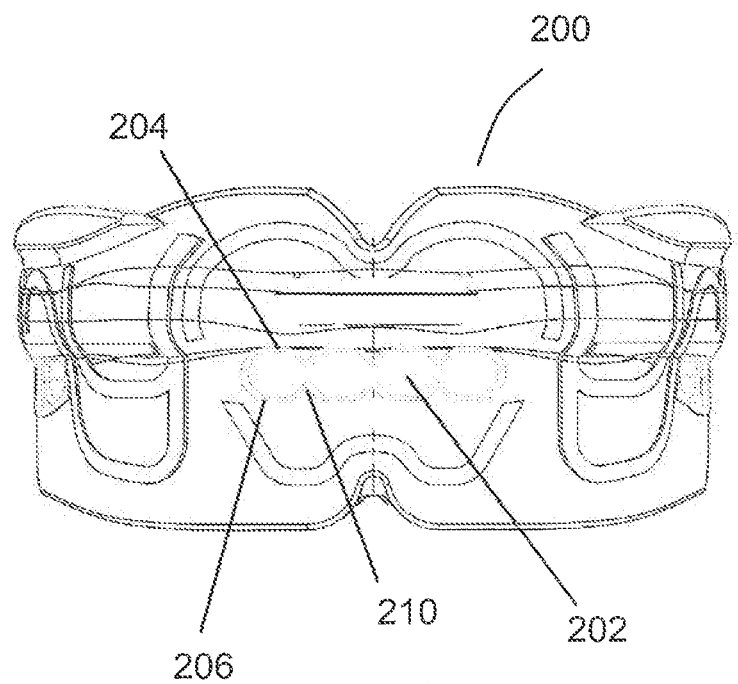
FIG. 14 is a front view of a further embodiment of an oral appliance in a first hole configuration and FIG. 15 is a front view of the oral appliance shown in FIG. 14 in a second hole configuration.
Figure 15:
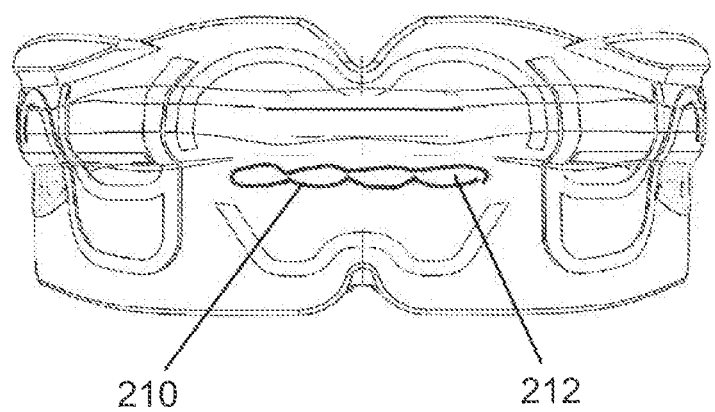

FIGS. 14 and 15 show an alternative appliance 200. The appliance is made from a soft silicone material that is compressible when the user bites down upon the appliance. FIG. 14 shows the appliance in the uncompressed or passive configuration.

The appliance 200 has a single longitudinal breathing hole 202 at the front of the appliance, rather than a series of holes. The hole 202 is defined by an upper wall 204, a lower wall 206 and curved end walls 208. Each of the upper and lower walls 204, 206 has opposed projections 210 that extend into the breathing hole 202.

FIG. 15 shows the appliance 200 in the compressed state in which a user has bite down upon the appliance 200. This has the effect of compressing the web and drawing the upper and lower walls 204, 206 towards each other until the respective pairs of opposed projections abut each other and the web cannot be compressed any further. The respective pairs of abutted projections 210 define four smaller breathing holes 212.

The cross sectional area of breathing of the four breathing holes 212 in the compressed configuration is about 50% of the cross sectional area for breathing of the breathing hole 202 in the passive configuration.

The cross sectional area for breathing in the compressed configuration is close to or is the same as the cross sectional area for breathing of the next stage appliance. After a period of time of using the appliance without compression, the patient is taught to compress the holes for a period of time when awake. This reduces the amount of air that is being inhaled through the mouth and encourages nasal breathing. This encourages a smooth transition to the next stage appliance.

It may be appreciated that there are many surprising and unexpected advantages of the disclosed appliances and disclosed methods. The silicone appliances do not require boil and bite or custom fitting, they are flexible, comfortable and have a degree of compression so as to alleviate stress on the TMJ. The tongue tag causes the tongue to project forward and therefore further assists in opening the pharyngeal airway. This may mean that it may not be necessary to over advance the mandible to the same extent as prior art MAD devices. This means that there is less discomfort and more importantly less likelihood of TMJ damage. The devices as disclosed herein may therefore be safely used in children. Further the tongue tag can stimulate tongue activity that may improve tongue strength to hold it in the maxilla and holding the mandible forward.

Most importantly is that the presently disclosed appliances and methods allow for retraining a patient to breathe through the nose, thereby alleviating and addressing the underlying problem of SBD that is caused by and associated with mouth breathing.

Even further, the disclosed appliances and methods allow the blood buffering ability and homeostatic set points to return to normal. This addresses the hyperventilative symptoms. Blood pH is at the optimum level for release of $O_2$ to the cells. Arterial diameter is also normal in return to a normal pH.

It will be appreciated that the present appliances can provide such benefits within about eight to about eighteen months of treatment. This may be compared to long term and continued use that is required by art known MAD and tongue retaining devices.

Whilst such devices may alleviate snoring by physically advancing the mandible and opening the airways and preventing airway collapse, they do nothing to increase $O_2$ supply to the cells. A person wearing a MAD device will continue presenting hyperventilative symptoms. Ongoing use of such devices may result in TMJ damage, and changes in bite and occlusion.

It will be appreciated that various changes and modifications may be made to the appliances and methods as disclosed herein without departing from the spirit and scope thereof.

The invention claimed is:

1. A set of oral appliances for treating sleep disorder breathing in a patient comprising,
   a first oral appliance for use in a first stage of treatment,
   a second oral appliance for use in a second stage of treatment,
   and at least a third oral appliance for use in at least a third stage of treatment,
   wherein each of the first oral appliance, the second oral appliance, and the at least third oral appliance comprises:
   a generally U shaped appliance body with a front section and two arms, the appliance body including an inner wall and an outer wall;
   a web interconnecting the inner wall and the outer wall;
   the inner and outer walls each have an upper portion that projects above the web so as to define an upper dental arch receiving channel;
   the inner and outer walls each have a lower portion that depends below the web that defines a lower dental arch receiving channel; and
   wherein the web comprises at least one breathing hole so as to define a total cross sectional area for breathing and the total cross sectional area for breathing of the first oral appliance is larger than the total cross sectional area for breathing of the second oral appliance, the total cross sectional area available for breathing in the third oral appliance is less than that of the total cross sectional area available for breathing in the second oral appliance; and
   wherein the web of the first oral appliance has a web thickness adapted to prevent lips of the patient from closing over the at least one breathing hole, the second oral appliance has a web thickness that is less than the web thickness of the first oral appliance, and the third oral appliance has a web thickness that is adapted to allow lips of the patient to close over the at least one breathing hole,
   wherein sequential use of the first oral appliance, the second oral appliance, and the at least third oral appliance increases a restriction of air flow in the patient's breathing to transition a relatively greater quantity of airflow to travel through the patient's nasal passage than through the patient's mouth.

2. The set of oral appliances of claim 1, wherein the first oral appliance includes a tongue elevator for lifting the tongue towards the patient's maxilla and a first distance is defined between the tongue elevator and the upper dental arch receiving channel, the second oral appliance includes a tongue elevator for lifting the tongue towards the patient's maxilla and a second distance defined between the tongue elevator and the upper dental arch receiving channel and the first distance is greater than the second distance, the at least third oral appliance includes a tongue elevator for lifting the tongue towards the patient's maxilla and a third distance is defined between the tongue elevator and the upper dental arch receiving channel and the second distance is greater than the third distance.

3. The set of oral appliances of claim 1, wherein the set of oral appliances includes 4 to 6 oral appliances, and wherein each oral appliance comprises a different total cross sectional breathing area, and each oral appliance used in each stage of treatment has a total cross sectional breathing area that is less than the total cross sectional breathing area used in a previous stage of treatment.

4. The set of oral appliances of claim 3, wherein the oral appliance used in a final stage of treatment has at least one breathing hole with a diameter or width of about 1 mm or less.

5. The set of oral appliances of claim 3, wherein the upper and lower dental arch receiving channels of the first oral appliance are configured so that when the first oral appliance is worn in the patient's mouth, the patient's mandible is advanced to define a first degree of mandibular advancement, the upper and lower dental arch receiving channels of the second oral appliance are configured so that when the second oral appliance is worn in the mouth, the patient's mandible is advanced to define a second degree of mandibular advancement and the first degree of mandibular advancement is greater than the second degree of mandibular advancement and the upper and lower dental arch receiving channels of the third oral appliance are configured so that when the oral appliance is worn in the mouth, the patient's mandible is not advanced.

6. A set of oral appliances for treating sleep disorder breathing in a patient comprising:
   a first oral appliance and at least a second oral appliance, wherein each of the first and at least second oral appliance comprises:
   a generally U shaped appliance body with a front section and two arms, the appliance body including an inner wall and an outer wall;
   a web interconnecting the inner wall and the outer wall;
   the inner and outer walls each having an upper portion that projects above the web so as to define an upper dental arch receiving channel;
   the inner and outer walls each having a lower portion that depends below the web that defines a lower dental arch receiving channel;
   wherein the web comprises at least one breathing hole so as to define a total cross sectional area for breathing and the total cross sectional area for breathing of the first oral appliance is larger than the total cross sectional area for breathing of the at least second oral appliance; and
   wherein the upper portion of the inner wall of the first oral appliance defines a tongue tag that includes a central substantially rounded resilient section, of the at least second oral appliance also has a tongue tag with a rounded resilient section and the rounded resilient section of the second oral appliance is thinner than the rounded resilient section of the first oral appliance,
   wherein sequential use of the first oral appliance and the at least second oral appliance increase a restriction of air flow in the patient's breathing to transition a relatively greater quantity of airflow to travel through the patient's nasal passage than through the patient's mouth.

* * * * *